United States Patent [19]

Fuchs et al.

[11] 4,284,645

[45] Aug. 18, 1981

[54] 3-CHLOROSTYRYL-2,2-DIMETHYL-CYCLO-PROPANECARBOXYLIC ACID 4-FLUORO-3-PHENOXY-α-CYANO-BENZYL ESTERS AND THEIR USE AS ECTOPARASITICIDES

[75] Inventors: Rainer Fuchs; Wilhelm Stendel, both of Wuppertal, Fed. Rep. of Germany

[73] Assignee: Bayer Aktiengesellschaft, Leverkusen, Fed. Rep. of Germany

[21] Appl. No.: 77,502

[22] Filed: Sep. 20, 1979

[30] Foreign Application Priority Data

Oct. 11, 1978 [DE] Fed. Rep. of Germany ....... 2844271

[51] Int. Cl.$^3$ .................... A01N 53/00; C07C 121/75
[52] U.S. Cl. ................................. 424/304; 260/465 D
[58] Field of Search .................... 260/465 D; 424/304

[56] References Cited

U.S. PATENT DOCUMENTS

| | | |
|---|---|---|
| 3,973,036 | 8/1976 | Hirano et al. . |
| 4,110,360 | 8/1978 | Sheldon et al. .................. 260/465 D |
| 4,157,447 | 6/1979 | Engel ........................................ 560/8 |

*Primary Examiner*—Dolph H. Torrence
*Attorney, Agent, or Firm*—Sprung, Felfe, Horn, Lynch & Kramer

[57] ABSTRACT

3-Chlorostyryl-2,2-dimethyl-cyclopropanecarboxylic acid 4-fluoro-3-phenoxy-α-cyano-benzyl esters, which are useful as agents for combating ectoparasites, and a process for their preparation are described.

8 Claims, No Drawings

3-CHLOROSTYRYL-2,2-DIMETHYL-CYCLO-PROPANECARBOXYLIC ACID 4-FLUORO-3-PHENOXY-α-CYANO-BENZYL ESTERS AND THEIR USE AS ECTOPARASITICIDES

The invention relates to certain new 3-chlorostyryl-2,2-dimethyl-cyclopropanecarboxylic acid 4-fluoro-3-phenoxy-α-cyano-benzyl esters, to a process for their preparation and to their use as agents for combating ectoparasites.

It is already known that certain cyclopropanecarboxylic acid phenoxybenzyl esters, for example 3-(2,2-dichloro-vinyl)-2,2-dimethyl-cyclopropanecarboxylic acid 3-phenoxy-α-cyano-benzyl ester, can be used for combating ectoparasites (see DE-OS (German Published Specification) No. 2,601,743).

However, the action of these compounds is not always satisfactory, especially in the case of low concentrations of active compound and when low amounts are used.

The present invention now provides, as new compounds, the 3-chlorostyryl-2,2-dimethyl-cyclopropanecarboxylic acid 4-fluoro-3-phenoxy-α-cyano-benzyl esters of the general formula

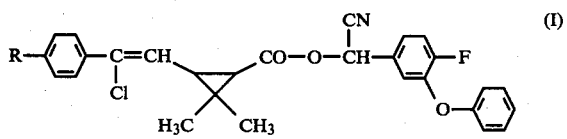

in which R represents hydrogen or fluorine.

The invention also provides a process for the preparation of a compound of the formula (I) in which a 3-chlorostyryl-2,2-dimethyl-cyclopropanecarboxylic acid chloride of the general formula

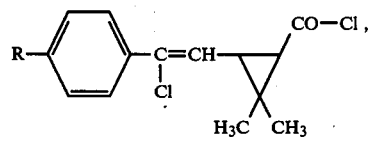

in which R has the meaning stated above, is reacted with 4-fluoro-3-phenoxy-benzaldehyde, which has the formula

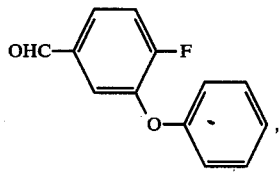

and at least an equimolar amount of an alkali metal cyanide (preferably sodium cyanide or potassium cyanide), if appropriate in the presence of a catalyst and if appropriate using a diluent.

The new 3-chlorostyryl-2,2-dimethyl-cyclopropanecarboxylic acid 4-fluoro-3-phenoxy-α-cyano-benzyl esters (I) are distinguished by a high activity against ectoparasites.

Surprisingly, the 3-chlorostyryl-2,2-dimethyl-cyclopropanecarboxylic acid 4-fluoro-3-phenoxy-α-cyano-benzyl esters according to the invention exhibit a considerably higher ectoparasiticidal action than compounds of similar structure and the same type of action which are known from the state of the art.

If, for example, 3-(2-chloro-2-phenyl-vinyl)-2,2-dimethyl-cyclopropanecarboxylic acid chloride, 4-fluoro-3-phenoxy-benzaldehyde and sodium cyanide are used as starting substances, the reaction of these compounds can be outlined by the following equation:

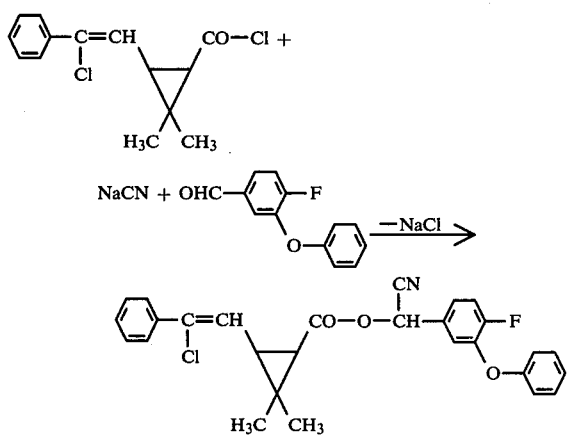

The 3-chlorostyryl-2,2-dimethyl-cyclopropanecarboxylic acid chlorides to be used as starting compounds are known, or they can be prepared by processes analogous to known processes (see DE-OS (German Published Specification) No. 2,738,150).

The compounds of the formula (II) are 3-(2-chloro-2-phenyl-vinyl)-2,2-dimethyl-cyclopropanecarboxylic acid chloride and 3-(2-chloro-2-(4-fluoro-phenyl)-vinyl)-2,2-dimethyl-cyclopropanecarboxylic acid chloride.

The 4-fluoro-3-phenoxy-benzaldehyde to be employed as a further starting component is likewise known (see DE-OS (German Published Specification) No. 2,709,264).

The process for the preparation of the new compounds of the formula (I) according to the invention is preferably carried out using a suitable diluent (which term includes a solvent). Possible diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxan; ketones, such as acetone, methyl ethyl ketone, methyl isopropyl ketone and methyl isobutyl ketone; and nitriles, such as acetonitrile and propionitrile.

Of the diluents mentioned, those which are water-immiscible are preferably used, in combination with water as a second solvent component (to give a two-phase medium).

In general, a compound which usually serves as an auxiliary for the phase transfer of reactants in the case of reactions in multi-phase media is then used as a catalyst. Tetraalkyl-ammonium salts and trialkyl-aralkylammonium salts, for example tetrabutylammonium bromide and trimethyl-benzyl-ammonium chloride, may be mentioned in particular.

The reaction temperature can be varied within a substantial range. In general, the reaction is carried out at from 0° to 100° C., preferably at from 10° to 50° C. In general, the process according to the invention is carried out under normal pressure, but it can also be carried out under increased pressure.

The starting substances are usually employed in equimolar amounts for carrying out the process according to the invention. However, it is also possible to employ an excess of one or other of the reactants. In general, the reaction is carried out in one or more diluents in the presence of a catalyst, and the reaction mixture is stirred at the required temperature for several hours. The reaction product then may be isolated by known procedures. Preferably the reaction mixture is shaken with toluene/water and the organic phase is separated off, washed with water and dried. After distilling off the solvent, the new compounds are obtained as oils, which cannot be distilled without decomposition. However, they can be freed from the last volatile constituents by so-called "incipient distillation", that is to say by prolonged heating to moderately elevated temperatures under reduced pressure, and can be purified in this manner. The $^1$H-NMR spectra are used for their characterisation.

The active compounds of the general formula (I) and their salts have a powerful ectoparasiticidal action, in particular against Acarina, which, as animal ectoparasites, infest domestic animals, such as cattle, sheep and rabbits. At the same time, the active compounds of the general formula (I) have only a low toxicity towards warm-blooded animals. They are therefore very suitable for combating animal ectoparasites from the class of Acarina. Furthermore, however, they also have an action against other Acarina and against insects.

Examples which may be mentioned are: scab mites, lice and Diptera and their larvae.

As ectoparasites which are very important economically, especially in tropical and sub-tropical countries, there may be mentioned: the Australian and South American cattle tick *Boophilus microplus*, the South African cattle tick *Boophilus decoloratus*, both from the family of the Ixodidae, and other cattle ticks and sheep ticks.

In the course of time, ticks in particular have become resistant towards the phosphoric acid esters and carbamates hitherto used as agents for combating them, so that the success in combating them is becoming questionable to an increasing extent in many regions. To ensure profitable livestock husbandry in the infested regions, there is an urgent need for agents with which ticks in all stages of development, that is to say larvae, nymphs, metanymphs and adults, even of resistant strains, for example of the genus Boophilus, can be reliably combated. In Australia, the Mackay strain, the Biarra strain and the Mount Alford strain of *Boophilus microplus*, for example, are to a large extent resistant towards the phosphoric acid esters hitherto used.

The active compounds of formula (I) according to the invention have an equally good action both against the normally sensitive and against the resistant strains, for example of Boophilus. In a customary application to the host animal, they have both a direct action on all the parasitic forms on the animal and a powerful ovicidal action on the adult forms, so that the reproduction cycle of the ticks is interrupted both in the parasitic phase on the animal and in the non-parasitic phase. The laying of eggs is halted and the development and hatching are inhibited.

Depending on the envisaged form of application, the new active compounds can be converted into the formulations customary in practice, for example solutions, emulsions, suspensions, powders, pastes and granules. These may be produced in a known manner, for example by mixing the active compounds with extenders, that is to say liquid or solid diluents or carriers, optionally with the use of surface-active agents, that is to say emulsifying agents and/or dispersing agents. In the case of the use of water as an extender, organic solvents can, for example, also be used as auxiliary solvents if appropriate.

Examples of possible liquid diluents or carriers, especially solvents, are aromatics (for example xylene, benzene, ortho-dichlorobenzene and trichlorobenzene), paraffins (for example mineral oil fractions), alcohols (for example methanol, ethanol, isopropanol and butanol), strongly polar solvents (such as dimethylformamide, N-methyl-pyrrolidone and dimethylsulphoxide) as well as water.

Solid diluents and carriers which may be mentioned are ground natural minerals (for example kaolins, clays, talc and chalk) and synthetic inorganic carriers (for example highly-dispersed silicic acid and silicates).

Emulsifying agents which may be mentioned are non-ionic, anionic or cationic emulsifiers, for example polyoxyethylene-fatty acid esters and polyoxyethylene-fatty alcohol ethers (for example alkyl-aryl polyglycol ethers), alkyl-sulphonates, aryl-sulphonates and quaternary ammonium salts with relatively long alkyl radicals. Dispersing agents which may be mentioned are lignin sulphite waste liquors and methylcellulose.

The formulations in general contain from 0.1 to 95% by weight of active compound, preferably from 0.5 to 90% by weight.

The application forms are in general prepared from the formulations above by dilution with water. The concentration of active ingredient can be varied within a wide range, depending on the use form, and is usually from 10 to 50,000 ppm (g/g), preferably from 50 to 500 ppm. (g/g).

The use forms may be applied in the customary manner, for example by spraying, pouring on, misting or dipping.

Other auxiliaries or active compounds, such as disinfecting agents or specifically suitable insecticides, can also be admixed to the formulations or the ready-to-use preparations.

The aqueous solutions and emulsions of the active compounds according to the invention have a good stability under conditions found in practice, so that the ready-to-use application forms remain active for three months and longer, even on standing for a relatively long time and in a pH range of 7–9.

The present invention also provides an ectoparasiticidal composition containing as active ingredient a compound of the present invention in admixture with a solid or liquefied gaseous diluent or carrier or in admixture with a liquid diluent or carrier containing a surface-active agent.

The present invention also provides a method of freeing or protecting domesticated animals from ectoparasitical pests (especially acarids, for example ticks) which comprises externally applying to said animals a compound according to the present invention, in admixture with a diluent or carrier.

PREPARATIVE EXAMPLE

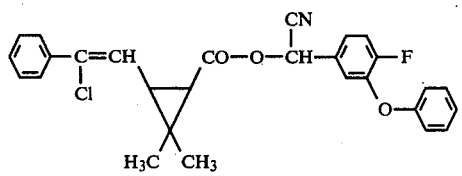

8.1 g (0.03 mole) of 3-(2-chloro-2-phenyl-vinyl)-2,2-dimethyl-cyclopropane-carboxylic acid chloride and 6.5 g (0.03 mole) of 4-fluoro-3-phenoxy-benzaldehyde are added dropwise to a mixture of 2.25 g of sodium cyanide, 3.5 ml of water, 150 ml of n-hexane and 0.75 g of tetrabutylammonium bromide at 20° to 25° C., whilst stirring. The reaction mixture is then stirred at 20° to 25° C. for 4 hours and is subsequently diluted with 300 ml of toluene and washed twice with 300 ml of water each time. The organic phase is dried over magnesium sulphate and the solvent is distilled off under a water-pump vacuum. Last residues of solvent are removed by brief incipient distillation at 60° C./1 mbar. 10.8 g (76% of theory) of 3-(2-chloro-2-phenyl-vinyl)-2,2-dimethyl-cyclopropanecarboxylic acid 4-fluoro-3-phenoxy-α-cyano-benzyl ester are obtained as a viscous oil.

The compound of the formula

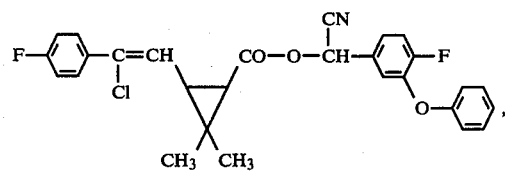

3-(2-chloro-2-(4'-fluorophenyl)-vinyl)-2,2-dimethyl-cyclopropanecarboxylic acid 4-fluoro-3-phenoxy-α-cyano-benzyl ester is obtained analogously, as a viscous oil, from 3-(2-chloro-2-(4'-fluorophenyl)-vinyl)-2,2-dimethyl-cyclopropanecarboxylic acid chloride and 4-fluoro-3-phenoxybenzaldehyde.

The structure of the two above-mentioned products is proved unambiguously by the ¹H-NMR spectra.

Characteristic ¹H-NMR data (CDCl₃/tetramethylsilane):

Compound (A)

Aromatic H: 2.30-3.15 τ (m/13H), benzyl H: 3.55-3.76 τ (m/1H), vinyl H: 4.0-4.38 τ (m/1H), cyclopropane H: 7.19-8.50 τ (m/2H) and dimethyl H: 8.50-8.9 τ (m/6H).

Compound (B)

Aromatic H: 2.28-3.21 τ (m/12H), benzyl H: 3.50-3.78 τ (m/1H), vinyl H: 4.1-4.43 τ (m/1H), cyclopropane H: 7.26-8.50 τ (m/2H) and dimethyl H: 8.50-9.0 τ (m/6H).

What is claimed is:

1. A 3-chlorostyryl-2,2-dimethyl-cyclopropanecarboxylic acid ester of the formula

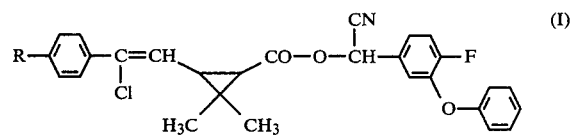

in which R represents hydrogen or fluorine.

2. A composition containing as active ingredient an ectoparasiticidally effective amount of a compound according to claim 1 in admixture with a solid or liquefied gaseous diluent or carrier or in admixture with a liquid diluent or carrier containing a surface-active agent.

3. A composition according to claim 2 containing from 0.1 to 95% of the active compound, by weight.

4. A method of freeing or protecting domesticated animals from ectoparasitical pests, which comprises externally applying to said animals an ectoparasiticidal amount of a compound according to claim 1 in admixture with a diluent or carrier.

5. A method according to claim 4 in which a composition is used containing from 10 to 50,000 ppm (g/g) of the active compound by weight.

6. A method according to claim 4 in which a composition is used containing from 50 to 500 ppm of the active compound, by weight.

7. A Method according to claim 4 in which the pests are acarids.

8. A method according to claim 7 in which the acarids are ticks.

* * * * *